United States Patent

Montefiori

[11] Patent Number: 4,472,180
[45] Date of Patent: Sep. 18, 1984

[54] APPARATUS FOR WITHDRAWING BLOOD FROM A TEST TUBE OR THE LIKE

[75] Inventor: Amerigo Montefiori, Rotkreuz, Switzerland

[73] Assignee: Guest Medical & Dental Products AG, Zug, Switzerland

[21] Appl. No.: 470,570

[22] Filed: Feb. 28, 1983

[30] Foreign Application Priority Data

Mar. 9, 1982 [CH] Switzerland ............... 1422/82

[51] Int. Cl.³ ............... B04B 9/12; C01G 9/00; C01G 23/00
[52] U.S. Cl. ............... 55/159; 128/760; 210/927; 210/513; 604/203; 604/231
[58] Field of Search ............... 55/159; 128/760, 403; 604/231, 203; 210/927, 513; 73/323, 290 R; 116/227

[56] References Cited

U.S. PATENT DOCUMENTS 4,279,863  7/1981  Friehler ............... 210/927

Primary Examiner—Frank Sever
Attorney, Agent, or Firm—Peter K. Kontler

[57] ABSTRACT

Blood is transferred from a test tube having a supply of blood covered by a head of foamed blood into a second tube which is provided with a graduated scale and both ends of which are open. An apparatus for performing the transfer includes a cap having a sleeve which is frictionally attached to and surrounds one end portion of the second tube. The cap further includes a bottom wall which is spaced apart from the end face of the one end portion of the second tube, a nipple which extends from the bottom wall in a direction away from the second tube, and an elastic sealing element which surrounds the sleeve and can slide along the internal surface of the test tube toward the supply of blood therein. The nipple defines a portion of a first path wherein the resistance to the flow of blood is much less pronounced than the resistance to the flow of foam along a second path which is defined by the cap in a region adjacent to the bottom wall. This ensures that the second path permits the escape of air from the interior of the test tube into the second tube while the nipple penetrates through the head of foam and into the supply of blood below such head. The flow of a solid column of blood into the second tube along the first path takes place as soon as the intake end of the second path is immersed into the foam. The minimal cross-sectional area of the second path is less than one fourth of the minimal cross-sectional area of the first path, and neither of these paths is wide enough to permit the penetration of foam. The column of blood in the second tube can be used for determination of the speed of descent of red blood cells. Since the second tube receives only a solid column of blood, the upper end of such column can be brought into accurate register with a selected graduation on the second tube.

22 Claims, 2 Drawing Figures

APPARATUS FOR WITHDRAWING BLOOD FROM A TEST TUBE OR THE LIKE

BACKGROUND OF THE INVENTION

The present invention relates to apparatus for transferring blood into a tube, and more particularly to an apparatus which can be utilized to ascertain the velocity of descent of red blood cells in a tube which is provided with a graduated scale.

Apparatus of the type to which the present invention pertains is disclosed, for example, in Swiss Pat. No. 417,158. As a rule, a supply of blood is introduced into a vessel from which the blood is transferred into the aforementioned tube. Problems arise in connection with the transfer of accurately metered quantities of blood into the tube because the supply of blood in the vessel is normally covered by a head of foamed blood. One end of the preferably cylindrical vessel is open to allow for insertion of one end portion of the tube whereby the foam penetrates into the tube together with blood and prevents the blood from forming a clearly defined meniscus at a desired level, e.g., in register with the zero graduation of a scale on the tube. One end portion of the tube is introduced into the vessel not unlike a piston into a cylinder whereby the head of foam invariably enters the tube and obscures the exact locus of the top level of the solid column of blood in the tube.

OBJECTS AND SUMMARY OF THE INVENTION

An object of the invention is to provide an apparatus which ensures that a tube can draw a solid column of blood from a vessel wherein the supply of blood is covered with a head of foamed blood.

Another object of the invention is to provide an apparatus which is simple, compact and inexpensive, which can withdraw solid columns of blood as often as desired, and whose operation is not affected by the height of the head of foam on top of the supply of blood.

An additional object of the invention is to provide an apparatus of the above outlined character which can employ a conventional graduated tube and can draw solid columns of blood from a conventional vessel.

A further object of the invention is to provide an apparatus with novel and improved means for preventing penetration of foam into the tube while the tube is caused to advance into a vessel which contains a supply of blood and a head of foamed blood on top of such supply.

Still another object of the invention is to provide a novel and improved method of transferring a solid column of blood from a vessel, wherein a supply of blood is covered by a head of foamed blood, into a tube.

A further object of the invention is to provide the apparatus with novel and improved means for permitting escape of air from the vessel during introduction of the tube.

Another object of the invention is to provide an apparatus which can be reused as often as desired, which can be readily taken apart for cleaning, and which can be reassembled with little loss in time.

The invention is embodied in an apparatus which can be used as a means for determining the speed of descent of red blood cells. The apparatus comprises an elongated tube whose length can exceed 200 mm and which has open first and second end portions and a graduated scale. The tube can be made of a light-transmitting material. The apparatus further comprises a cap having a preferably cylindrical sleeve which surrounds and is in frictional engagement with one end portion of the tube. The cap defines a first and a preferably shorter second path for the flow of a fluid into the tube by way of the one open end portion. The fluid which enters the tube by flowing along the first path encounters a resistance which is only a fraction of the resistance offered to the fluid that tends to flow into the tube along the second path. The cap preferably further comprises a radially deformable elastic sealing element which spacedly surrounds the one end portion of the tube; such sealing element can constitute a hollow conical frustum the smaller-diameter end of which is integral with the sleeve and the larger diameter end of which spacedly surrounds the tube between the first and second end portions.

The cap comprises a bottom wall which is adjacent to but spaced from the end face of the one end portion of the tube, and an elongated nipple which is provided on the bottom wall and extends beyond the latter in a direction away from the end face of the one end portion of the tube. The nipple defines the narrowest portion of the first path, and the cap further includes an apertured portion which is disposed in the region of the bottom wall and defines the second path.

The minimum cross-sectional area of the second path is preferably a minute fraction of the minimum cross-sectional area of the first path; for example, the minimum cross-sectional area of the second path should not exceed one-fourth of the minimum cross-sectional area of the first path. At least one distancing element is preferably interposed between the bottom wall of the cap and the end face of the one end portion of the tube; such distancing element can form part of the cap and its purpose is to ensure that the one portion of the tube and the bottom wall define at least one clearance which forms part of at least one of the two paths. The end face of the one end portion of the tube can abut directly against the distancing element.

The nipple is preferably offset with reference to the axis of the tube, as considered in the radial direction of the one end portion of the tube, and that portion of the first path which is defined by the nipple is preferably aligned with a portion of the end face of the one end portion of the tube. The narrowest portion of the second path can also be aligned with a portion of the end face of the one end portion of the tube.

The apparatus further comprises a vessel (e.g., a cylinder one end of which is open) which is arranged to confine a supply of blood and a head of foam on top of the supply of blood. When the cap is inserted into the vessel through the latter's open end, the aforementioned sealing element slides along the internal surface of the cylinder while the nipple approaches and penetrates through the head of foam on its way into the supply of blood. At such time, the shorter second path allows for escape of air from the region above the head of foam. When the open end of the second path penetrates into the head of foam, the outflow of air is terminated and blood can rise along the first path to enter the tube while the second path prevents the inflow of foam because its resistance to the flow of fluids is a multiple of the resistance of the first path. This ensures that the tube accumulates a column of blood which is free of foam so that the location of the meniscus on top of the column of blood in the tube can be ascertained (with resort to the aforementioned scale) with a very high degree of accuracy.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain specific embodiments with reference to the accompanying drawing.

DESCRIPTION OF THE PREFERRED EMBODIMENTS

Figure 1:
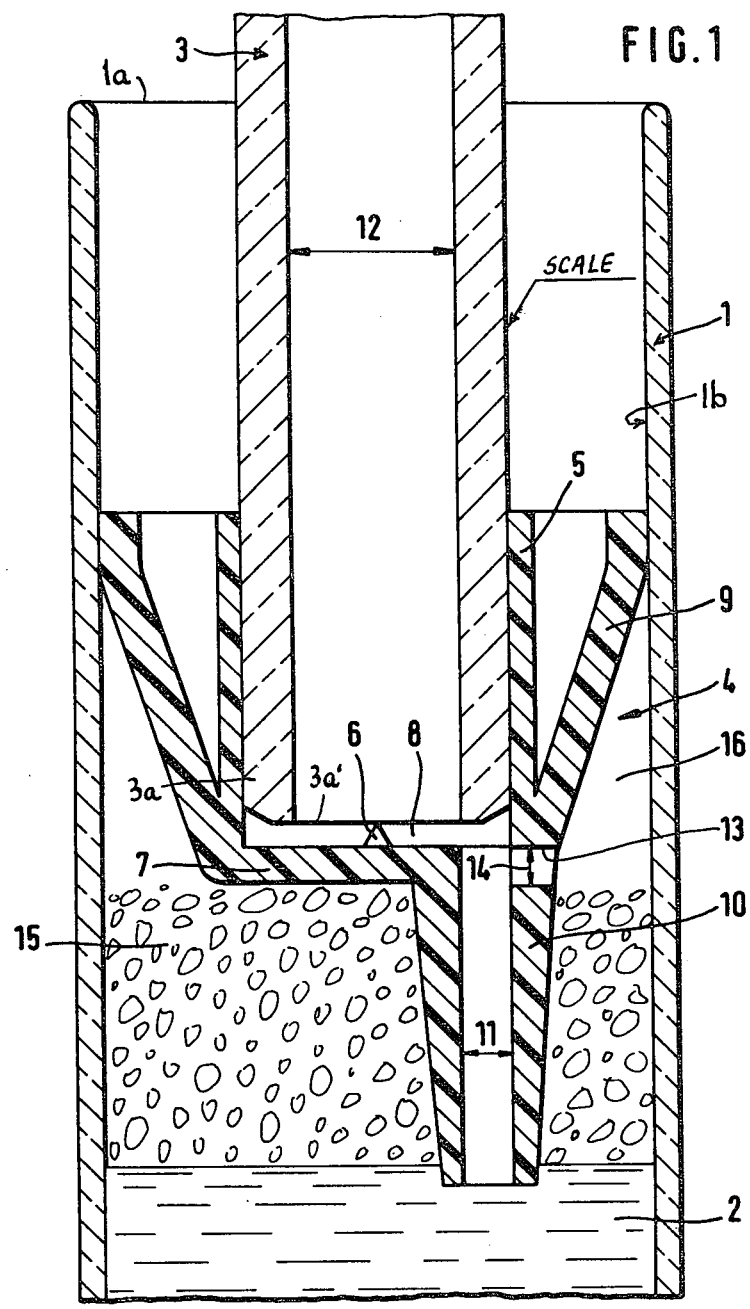
FIG. 1 is a fragmentary axial sectional view of an apparatus which embodies one form of the invention, with the cap in a position in which the nipple can draw blood while the open end of the shorter path is about to reach the head of foam on top of the supply of blood.

FIG. 1 shows a portion of an apparatus which comprises a preferably cylindrical upright test tube-like vessel 1 having an open upper end (at 1a) and a closed bottom, not shown. The vessel 1 contains a supply or pool 2 of blood and a head 15 of foam on top of the supply 2.

The apparatus further comprises an elongated tube 3 whose material is transparent or translucent, at least in the region of a graduated scale which is indicated by a legend. The two end portions of the tube 3 are open; FIG. 1 merely shows the open lower end portion 3a having an annular end face 3a' which is spaced apart from the upper side of the bottom wall 7 of a closure or cap 4. The latter further includes a cylindrical sleeve 5 which surrounds and frictionally engages the lower end portion 3a of the tube 3. The lower end portion of the sleeve 5 is integral with the peripheral portion of the bottom wall 7 as well as with the smaller-diameter lower end of a hollow frustoconical sealing element 9 whose larger-diameter upper end is in frictional engagement with the internal surface 1b of the vessel 1. Still further, the cap 4 includes an elongated nipple 10 which is integral with and extends downwardly beyond the underside of the bottom wall 7, i.e., in a direction away from the end face 3a' of the end portion 3a. The nipple 10 defines the narrowest part of a relatively long first path which allows blood to flow from the supply 2 in the vessel 1 into the tube 3 by way of the lower end portion 3a. To this end, the end face 3a' of the end portion 3a defines with the upper side of the bottom wall 7 an annular clearance 8 which communicates with the passage in the nipple 10 as well as with the interior of the tube 3.

A portion 13 of the cap 4 is disposed at the general level of the bottom wall 7 and has an aperture so that it defines the narrowest portion of a second path for the flow of a fluid from the interior of the vessel 1 into the interior of the tube 3. The second path is shorter than the first path and can actually merge into that portion of the first path which is defined by the uppermost part of the nipple 10. The width of the clearance 8 is established by a distancing element 6 which forms part of the cap 4 and extends upwardly from the inner side of the bottom wall 7. The latter can carry two or more distancing elements.

The cross-sectional area of the passage in the nipple 10 is preferably constant from end to end, and such passage can be bounded by a cylindrical internal surface of the nipple. It will be noted that the diameter 11 of the passage in the nipple 10 is much smaller than the inner diameter 12 of the tube 3.

The aperture of the cap portion 13 is preferably also bounded by a cylindrical surface, and the diameter 14 of such aperture is smaller than that (11) of the passage in the nipple 10. Thus, the second path which is defined by the portion 13 offers a greater resistance to the flow of fluid into the tube 3 than the first path the narrowest portion of which is defined by the nipple 10. The arrangement is preferably such that the minimal cross-sectional area of the second path at most equals one-fourth of the minimal cross-sectional area of the first path. It can be said that the first path includes the passage in the nipple 10 as well as the clearance 8, whereas the second path includes the aperture in the cap portion 13, a portion of the passage in the nipple 10 and the clearance 8. The narrowest portion of the second path is the aperture in the portion 13, and the narrowest portion of the first path is the passage of the nipple 10.

The operation is as follows:

The vessel 1 is assumed to contain a supply 2 of blood to be tested and a head 15 of foamed blood on top of the supply 2. Such head develops in response to pouring of blood into the vessel 1 or even before. In the next step, the cap 4 is introduced into the open unner end 1a of the vessel 1 so that the larger-diameter end of the sealing element 9 slides along the internal surface 1b of the vessel and the cap pushes a column of air downwardly toward the head 15. Such air can escape from the space 16 below and around the lower part of the sealing element 9 by flowing along each of the two paths which are defined by the cap 4. The diameter 11 of the passage in the nipple 10 is sufficiently small to prevent the rise of a column of foam therein so that the lower end portion of the nipple 10 passes through the head 15 and ultimately penetrates into the supply 2 of unfoamed body fluid. Once the lower end portion of the nipple 10 penetrates into the head 15, air from the space 16 above th e head 15 escapes only along the second path, i.e., through the aperture of the cap portion 13, the upper portion of the passage in the nipple 10 and the clearance 8, to rise into the lower end portion 3a and thence into the upper part of the tube 3. Blood from the supply 2 begins to rise in the nipple 10 and to flow into the clearance 8 as soon as the portion 13 of the cap 4 is immersed into the head 15 of foamed body fluid. The foam cannot penetrate through the aperture of the cap portion 13 because the diameter 14 of this aperture is much smaller than the diameter 11 of the passage in the nipple 10. As mentioned above, the second path of the cap 4 offers a very pronounced resistance to the flow of a fluid therealong, namely, a resistance which is much higher than that of the first path. This is the reason that foam cannot enter the second path while the first path allows for penetration of a solid column of blood into the tube 3. However, the second path allows for escape of air from the space 16 into the surrounding atmosphere via tube 3 as long as the portion 13 is not immersed into the head 15 of foam above the supply 2 of liquid. Since the tube 3 receives only a solid column of blood, the meniscus at the upper end of such column is readily detectable and the admission of blood into the tube 3 can be terminated when the upper end of the column reaches a predetermined graduation of the scale.

It will be noted that the passage of the nipple 10 is in line with a portion of the end face 3a' of the lower end portion 3a of the tube 3. Also, the aperture of the cap portion 13 is at least close to being in line with a portion of the end face 3a'. In other words, the bottom wall 7 of the cap 4 is in register with practically the entire opening which is surrounded by the end face 3a'. This ensures that one can readily achieve in the tube 3 a measuring path of 200 mm as required by Westergren.

The cap 4 can have two or more apertured portions 13 without departing from the spirit of the invention. All that counts is to ensure that a fluid which tends to enter the tube along one or more second paths encounters a much greater resistance than a fluid which is to enter the tube 3 along the first path.

Figure 2:
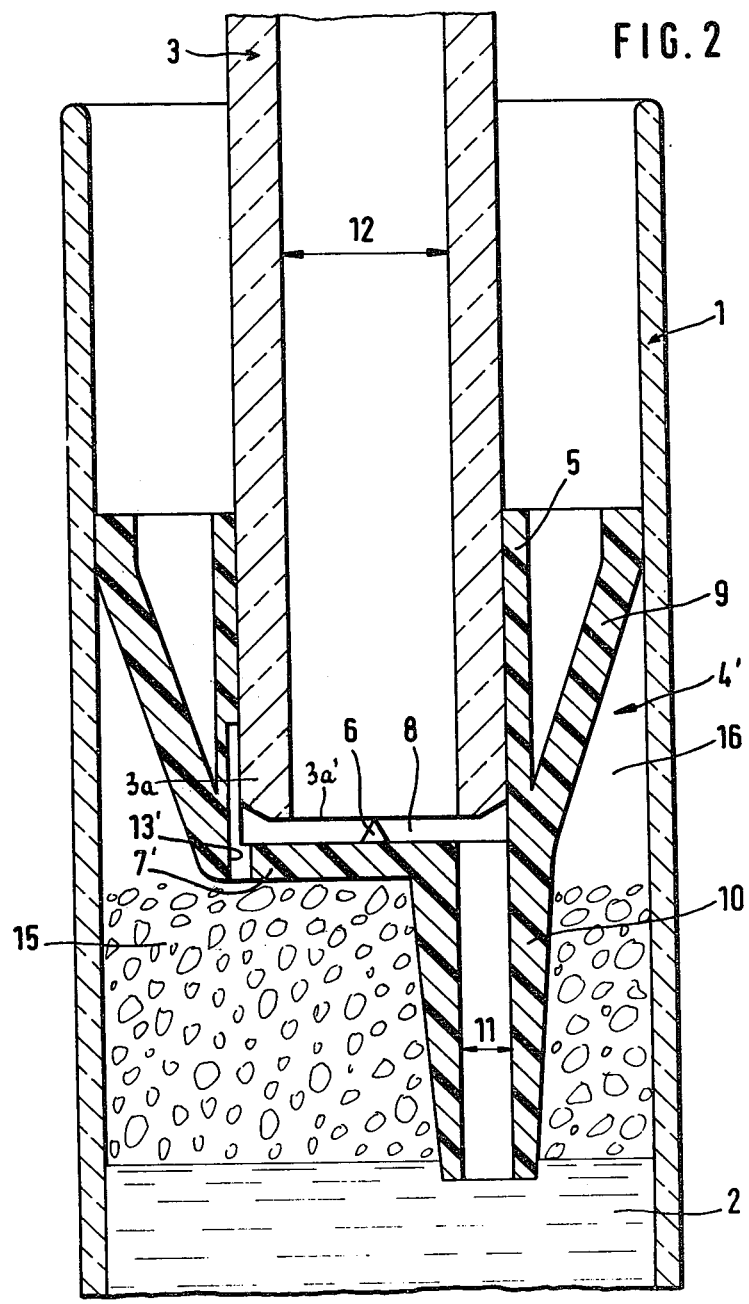
FIG. 2 is a similar fragmentary axial sectional view of a modified apparatus.

FIG. 2 shows a portion of a second apparatus wherein all such parts which are identical with or clearly analogous to the corresponding parts of the first apparatus are denoted by similar reference characters. The main difference between the two apparatus is that the apertured portion 13' of the cap 4' is provided in the bottom wall 7' and is clearly in line with a portion of the end face 3a' of the lower end portion 3a of the tube 3. Thus, the narrowest portion of the second path is transferred to a location substantially diametrically opposite the nipple 10 with reference to the axis of the tube 3. Therefore, the second path is defined solely by the aperture of the portion 13' and by the clearance 8 between the bottom wall 7' and the end face 3a' of the lower end portion 3a. Again, the minimal cross-sectional area of the second path is only a small fraction of the minimal cross-sectional area of the first path which is defined by the passage of the nipple 10 and the clearance 8.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. A structure for metering blood comprising: means for accurately metering samples of blood having a foam layer thereon, comprising means for collapsing and venting only air from said foam layer including
   (a) a tube having at least one open end portion; and
   (b) an elastically deformable cap mounted on said tube at said one end portion and having two passages which connect the interior of said tube with the surroundings via said one end portion, said passages opening to the surrounding at respective locations which are spaced in the axial direction of said tube, and one of said passages offering a higher resistance to fluid flow than the other of said passages.

2. The structure of claim 1, wherein said cap includes a sleeve which surrounds and is in frictional engagement with said one end portion of the tube.

3. The structure of claim 2, wherein said sleeve is a cylinder.

4. The structure of claim 1, wherein said cap comprises a radially deformable elastic sealing element spacedly surrounding said one end portion of the tube.

5. The structure of claim 1, wherein said one end portion of the tube has an end face and said cap comprises a bottom wall adjacent to said end face, said cap further comprising an elongated nipple extending beyond said bottom wall in a direction away from said end face and defining said other passage.

6. The structure of claim 5, wherein said cap has an apertured portion disposed in the region of said bottom wall and defining said one passage.

7. The structure of claim 1, wherein the minimum cross-sectional area of said one passage at most equals one-fourth of the minimum cross-sectional area of said other passage.

8. The structure of claim 1, wherein said cap includes a hollow frustoconical sealing element which is elastically deformable radially of said tube and spacedly surrounds said one end portion.

9. The structure of claim 8, wherein said cap further comprises a sleeve surrounding and frictionally engaging said one end portion, said sealing element having a smaller-diameter end integral with said sleeve and a larger-diameter end spacedly surrounding said tube between the end portions thereof.

10. The structure of claim 1, wherein said cap includes a bottom wall facing said one end portion of the tube, and further comprising at least one distancing element interposed between said one end portion and said bottom wall so that the bottom wall and the one end portion define a clearance communicating with at least one of said passages.

11. The structure of claim 10, wherein said distancing element forms part of said cap, said one end portion having an end face abutting against said distancing element.

12. The structure of claim 1, wherein said cap includes a bottom wall adjacent to and facing said one end portion of the tube and a nipple defining said other passage, said nipple being offset with reference to the axis of said tube, as considered radially of said one end portion, said one end portion having an end face adjacent to said bottom wall and said other passage being aligned with a portion of said end face.

13. The structure of claim 1, wherein said one end portion of the tube has an end face and a portion of said one passage is aligned with a portion of said end face.

14. The structure of claim 1, wherein said tube has a graduated scale.

15. The structure of claim 1, wherein said other passage is longer than said one passage.

16. The structure of claim 1, further comprising a vessel arranged to contain a supply of blood and a head of foam on top of such supply, said cap being insertable into said vessel so that said other passage allows the blood to flow from the supply into said tube while said one passage extends into the head of foam in said vessel.

17. The structure of claim 16, wherein said vessel is a cylinder having an open end and said cap comprises a radially deformable elastic sealing element surrounding said one end portion of the tube and arranged to slide along the internal surface of the vessel in response to introduction of the cap into said vessel through the open end of the latter.

18. The structure of claim 1, wherein the length of said tube is at least 200 mm.

19. The structure of claim 1, wherein said tube consists of a light-transmitting material.

20. The structure of claim 1, wherein the minimum cross-sectional area of said one passage is a minute fraction of the minimum cross-sectional area of said other passage.

21. The structure of claim 1, wherein the other end portion of said tube is open.

22. The structure of claim 1, wherein said one passage opens to the surroundings at a location nearer to said tube than the location at which said other passage opens to the surroundings.

* * * * *